United States Patent [19]

Segers

[11] Patent Number: Plant 7,244

[45] Date of Patent: Jun. 12, 1990

[54] **GERBERA PLANT (*GERBERA JAMESONII*) NAMED 'AMBER'**

[75] Inventor: Th. A. Segers, Hoofddorp, Netherlands

[73] Assignee: Twyford Plant Laboratories, Inc., Santa Paula, Calif.

[21] Appl. No.: 317,212

[22] Filed: Feb. 28, 1989

[51] Int. Cl.[5] ..... A01H 5/00

[52] U.S. Cl. ..... Plt./68

[58] Field of Search ..... Plt. 68

*Primary Examiner*—Howard J. Locker

*Attorney, Agent, or Firm*—Townsend and Townsend

[57] ABSTRACT

An original variety of Gerbera plant distinguished by a red color of its flowers, and its ability to grow vigorously and flower profusely during the spring, midseason, and fall blooming periods as well as blooming in the winter in the greenhouse.

1 Drawing Sheet

BACKGROUND OF THE PLANT

This Gerbera variety, named 'Amber', originated as a seedling at Rijsenhout, and resulted from the crossing in March of 1981 of 77-224 as the seed parent and the pollen parent identified as 78-822, taken from my collection of Gerbera maintained for breeding purposes at Rysenhout, the Netherlands. My objective in making the crossing being to develop new Gerbera varieties having blooms of good quality and excellent color on strong plants having good winter production in my greenhouses. This plant was selected from the seedlings resulting from the above crossing because of its extraordinary flower coloration and its vigorous and strong growth habit. The characteristics embracing the above objectives along with other desirable improvements as set forth below distinguish this new plant from its parents as well as from all other varieties of which I am aware.

The varieties thought to be most similar are 'Pamela', 'Gracia' and 'Chantal'. 'Amber' is distinguished from 'Pamela' by its more intense color and more numerous florets. 'Amber' is distinguished from 'Gracia' by its deeper purple and its wider florets. 'Amber' is distinguished from 'Chantal' by its different color, wider florets and greater production.

Asexual propagation of this selected plant was carried on under my direction at Rysenhout by cuttings and further by means of tissue culture at Naaldwijk, the Netherlands, through several successive generations which clearly demonstrated that the novel characteristics of its blooming and growth habits appear to be firmly fixed and will remain true from generation to generation.

The following is a detailed description of my new Gerbera plant based upon observations of greenhouse plants grown at Naaldwijk, Netherlands, the color designations being according to the R.H.S. Colour Chart published by the Royal Horticultural Society of London, England.

DESCRIPTION OF THE DRAWING

This new variety of *Gerbera jamesonii,* named 'Amber' is illustrated by the accompanying photographic drawing (FIG. 1) which shows its bloom in full color, with such colors of the photograph being as true to those of the plant as can be reasonably obtained from conventional professional photographic procedures.

DESCRIPTION OF THE PLANT

Leaf length: Short.
Leaf width: Medium.
Leaf blade thickness: Medium.
Leaf blade blistering: Weak.
Leaf blade pubescence on upper side mid-rib excluded: Medium.
Leaf blade depth of incisions on basal part: Deep.
Leaf blade depth of incisions on the central third: Medium to deep.
Leaf blade depth of incisions on distal part: Shallow.
Leaf blade color of upper side: Medium green RHS 139 A.
Leaf blade glossiness of upper side: Weak.
Leaf blade angle of apex: Weakly obtuse.
Leaf blade shape of apex: Pointed, very top rounded.
Leaf blade margin of lobes: Dentate.
Leaf blade extensions of margin: Medium.
Petiole length: Short.
Petiole anthocyanin coloration: Present.
Petiole intensity of anthocyanin coloration: Medium.

DESCRIPTION OF THE FLOWER

Peduncle length: Short.
Peduncle cross section: Round.
Peduncle tendency to fasciation: Absent.
Peduncle thickness: Medium.
Peduncle strength: Medium.
Peduncle pubescence: Medium to strong.
Peduncle color: Medium Green RHS 144 B.
Peduncle anthocyanin color at base: Present.
Peduncle intensity of anthocyanin coloration at base: Weak.
Peduncle anthocyanin coloration at top: Absent.
Peduncle involucral bracts: Absent.
Flower head type: Semi-Double.
Flower head diameter: Medium.
Flower head height from point of attachment of involucre to top of flower head: Medium.
Flower head height of involucre: Medium.
Flower head diameter of involucre: Medium.
Flower head number of involucral bracts: Few.
Flower head longitudinal axis of bracts of inner rows of involucre: Straight.
Flower head anthocyanin coloration at top of inner involucral bracts: Absent.

Flower head intensity of anthocyanin coloration at top of inner involucral bracts: N/A.

Flower head pubescence of involucre: Medium to Strong.

Flower head number of ray florets of outer rows: Few.

Flower head shape of ray florets of out row: Narrow elliptic.

Ray floret longitudinal axis of rays of outer row: Straight to Reflexing.

Ray floret longitudinal axis of rays of inner row (normally developed ray florets): Straight.

Female floret longitudinal axis of ray (outer ray florets excluded — semi-double or double varieties only): Incurving.

Male floret longitudinal axis of ray (semi-double or double varieties only): Incurving.

Outer ray floret cross section of ray: Flat.

Outer ray floret length: Long.

Outer ray floret width: Medium to Wide.

Outer ray floret longitudinal folding: Medium.

Outer ray floret angle of apex: Acute to right angle.

Outer ray floret shape of apex: Rounded.

Outer ray floret incisions of apex: Present.

Outer ray floret number of incisions: Two.

Outer ray floret depth of incisions: Medium.

Outer ray floret length of free petals: Medium to Long.

Outer ray floret color of inner side:

| Description | Remarks |
|---|---|
| RHS 44A or 46B | Base more diffused and very top creamy colored to red yellow RHS 18B. |

Outer ray floret distribution of the color on the inner side: Lighter towards the top.

Outer ray floret edge of different color: Absent.

Outer ray floret striation: Absent.

Outer ray floret color of outer side:

| Description | Remarks |
|---|---|
| RHS 2D<br>RHS 51B–C | Greenish yellow like RHS 2D, with Irregular diffused pink contract RHS 51B–C |

Outer ray floret claw spot: Present.

Disc diameter (single or semi-double varieties only): Medium.

Disc main color before flowering of disc florets (single or semi-double varieties only): Green RHS 145 A.

Disc main color of perianth lobes of female flowers: Red, reddish pink RHS 2D+51B.

DESCRIPTION OF REPRODUCTION ORGANS

Style main color of distal part: White RHS 11 D.

Stigma main color: Yellow RHS 2 D.

Anthers main color: Dark Yellow RHS 16 A.

Anthers color of top relative to other parts: Darker.

Anthers longitudinal stripes: Present, vaguely.

Pappus main color: Yellow RHS 145 A.

Pappus color of top relative to other parts: Identical.

Pappus level of top relative to closed disc florets: Same level to slightly above.

I claim:

1. The new distinct variety of Gerbera plant herein described and illustrated and identified by the characteristics enumerated above.

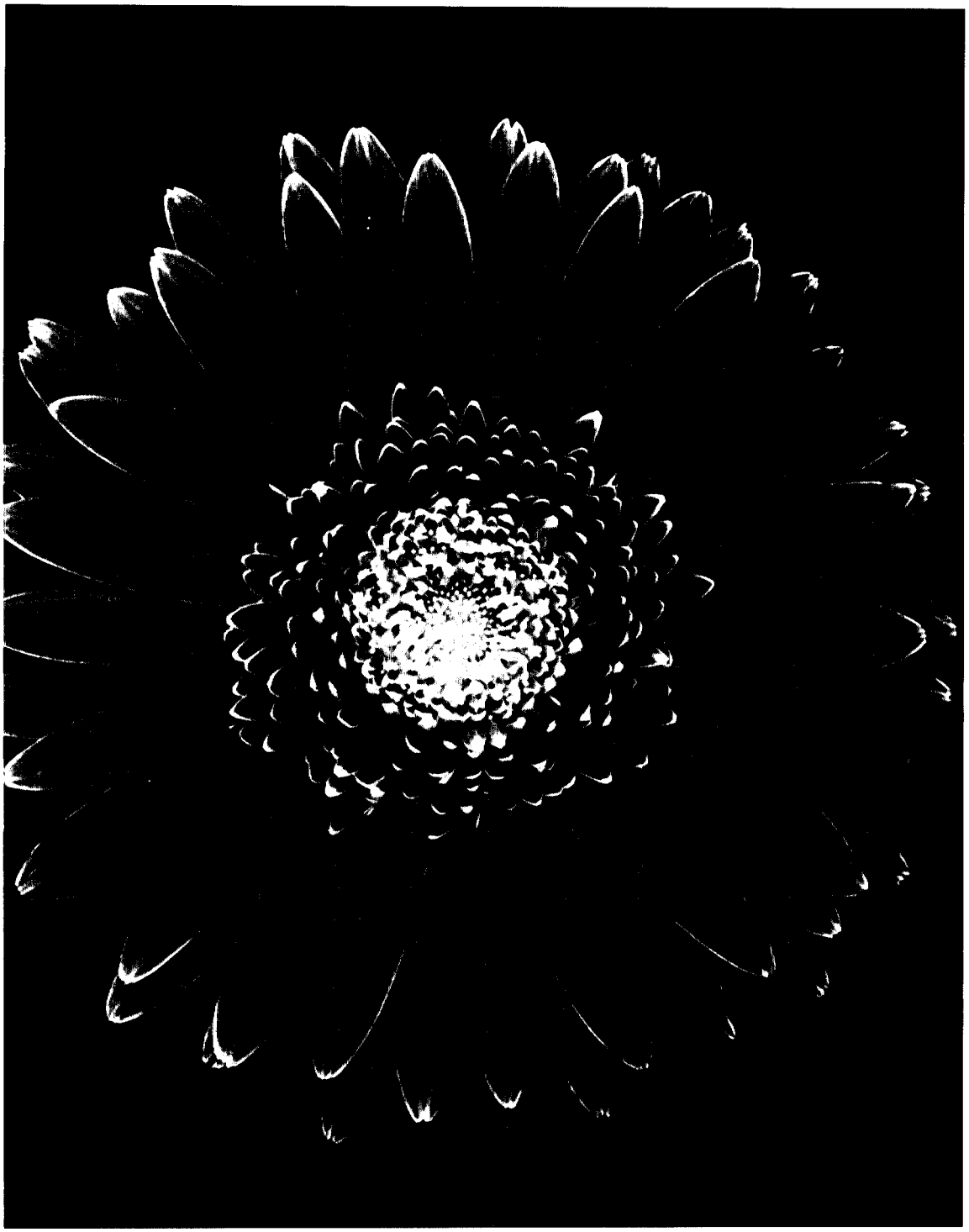

* * * * *